United States Patent
Cinar et al.

(10) Patent No.: US 12,337,080 B2
(45) Date of Patent: Jun. 24, 2025

(54) ANTIMICROBIAL ACTIVITY BY BEE BREAD AND THEIR PRODUCTION METHOD

(71) Applicant: BURSA TEKNIK UNIVERSITESI REKTORLUGU, Bursa (TR)

(72) Inventors: Aycan Cinar, Bursa (TR); Meral Akkoyun, Bursa (TR); Gokce Taner, Bursa (TR); Faruk Toktas, Bursa (TR)

(*) Notice: Subject to any disclaimer, the term of this patent is extended or adjusted under 35 U.S.C. 154(b) by 370 days.

(21) Appl. No.: 17/905,362

(22) PCT Filed: Mar. 2, 2021

(86) PCT No.: PCT/TR2021/050184
§ 371 (c)(1),
(2) Date: Aug. 31, 2022

(87) PCT Pub. No.: WO2021/177924
PCT Pub. Date: Sep. 10, 2021

(65) Prior Publication Data
US 2023/0098974 A1    Mar. 30, 2023

(51) Int. Cl.
*D01D 5/00*    (2006.01)
*A61L 15/26*   (2006.01)
*A61L 15/40*   (2006.01)
*A61L 15/44*   (2006.01)
*A61L 27/18*   (2006.01)
*A61L 27/36*   (2006.01)
*A61L 27/54*   (2006.01)

(52) U.S. Cl.
CPC .............. *A61L 27/54* (2013.01); *A61L 15/26* (2013.01); *A61L 15/40* (2013.01); *A61L 15/44* (2013.01); *A61L 27/18* (2013.01); *A61L 27/3637* (2013.01); *D01D 5/003* (2013.01); *A61L 2300/30* (2013.01); *A61L 2400/12* (2013.01); *D10B 2509/022* (2013.01)

(58) Field of Classification Search
CPC ..................................................... D01D 5/003
See application file for complete search history.

(56) References Cited

FOREIGN PATENT DOCUMENTS

| CN | 102119941 | * | 7/2011 |
| EP | 3072536 | * | 9/2016 |
| EP | 3569260 A1 | | 11/2019 |
| RU | 2365530 C2 | | 8/2009 |
| TR | 2019/09888 U5 | | 7/2019 |
| WO | 2015003155 A1 | | 1/2015 |
| WO | 2015079419 A1 | | 6/2015 |

OTHER PUBLICATIONS

International Search Report for corresponding PCT/TR2021/050184 dated May 30, 2021.
Written Opinion of the International Searching Authority for corresponding PCT/TR2021/050184 dated May 30, 2021.
Kim JI. et al., "Electrospun propolis/polyurethane composite nanofibers for biomedical applications", Materials Science & Engineering C (2014), Aug. 2, 2014.

* cited by examiner

*Primary Examiner* — Edmund H Lee
(74) *Attorney, Agent, or Firm* — Egbert, McDaniel & Swartz, PLLC

(57) ABSTRACT

Disclosed is a biocomposite product with high microbial activity obtained by using bee bread, the method of obtaining this product and using of this biocomposite material for the coating of products like artificial materials, packaging, etc. to be used in areas requiring hygiene or their use as an intermediate raw material.

15 Claims, No Drawings

ANTIMICROBIAL ACTIVITY BY BEE BREAD AND THEIR PRODUCTION METHOD

TECHNICAL FIELD

The invention mainly relates to natural products, in particular bee bread products, used in all fields that require antibacterial properties basically in food and health field.

In particular, the invention relates to the preparation of bee bread by extracting and lyophilizing, then mixing it with polymers to turn it into a biocomposite with high microbial activity in the form of nanofibers by electrospinning method and using the obtained biocomposite material as coating for products like artificial materials, packaging, etc. or their use as an intermediate raw material in areas requiring hygiene such as food and health.

PRIOR ART

Recently, natural products, especially bee products, have gained attention in scientific research. Current studies reveal that bee products such as honey species, royal jelly, propolis and pollen extract collected by honey bee have important functional and biological properties. It is reported that these products have very high antioxidant activity and free radical scavenging properties. Modern basic research shows that bee products are distinguished by their unique content of biologically active substances and act as biogenic stimulants, and their use in the food industry, apitherapy and pharmacology is increasing day by day (Kieliszek et al., 2018; Nagai et al., 2005).

Among such products, the popularity of pollen and bee bread is increasing. Bee bread is a product that has been known and used in traditional public health for many years and has attracted attention with its high nutritional value in recent years. Bee bread is a bee product made from pollen that is collected by the bees, mixed with digestive enzymes and carried back to the hive, made into pellets and protected with a small amount of honey and beeswax. The mixture prepared by bees undergoes different chemical processes under the influence of enzymes, microorganisms, humidity and temperature, and after 2 weeks it is called bee bread. Bee bread is the main source of proteins, lipids, microelements and vitamins for bees and is the most nutritious food. It contains 20% proteins, 3% lipids, 35% carbohydrates, 3% minerals and vitamins. Bee bread has a well-balanced protein content containing all essential amino acids and full spectrum vitamins (C, B1, B2, E, H, P, nicotinic acid, folic acid), as well as it contains pantothenic acid, pigments and enzymes such as sacchase, amylase, phosphatases, flavonoids and hormones. Bee bread contains more than 25 different micro and macro elements such as iron, calcium, phosphorus, potassium, copper, zinc, selenium, and magnesium. The composition of bee bread is slightly different than pollen. It has high acidity due to the presence of lactic acid and contains a greater amount of vitamin K. Lactic acid quality is six times higher than pollen. The high activity of bee bread ensures that the growth inhibition of molds as well as microorganisms so that it is well preserved (Nagai et al., 2005).

Nagai et al. (2005) showed the inhibitory activity of enzymatic hydrolysates obtained from bee bread on both antioxidant and angiotensin I-converting enzyme. Enzymatic hydrolysates were prepared from bee bread using three different proteases (pepsin, trypsin, and papain), and the antioxidant activities of these hydrolysates were measured using four different methods. Hydrolysates derived from bee bread have been reported to have a remarkable antioxidant activity similar or superior to that of 1 mm α-tocopherol. It has also been observed that has high scavenging activities against active oxygen species such as superoxide anion radical and hydroxyl radicals. It has also been found that it exhibits angiotensin I-converting enzyme inhibition activity. The data obtained from these studies have shown that hydrolysates obtained from bee bread are not only beneficial for healthy food diets, but can also be effective in patients with various diseases such as cancer, cardiovascular diseases, diabetes and hypertension.

Bee bread and propolis are among the bee products with high research potential and high commercial value in many countries with their benefits and uses.

In RU2365530 (C2), the product disclosed in the document was developed in order to expand the possibilities of efficient packaging of food products and medicines, in particular to allow the packaging itself to be used orally and sublingually. In this study, biologically active substances were added to the packaging material, including bee bread, by pre-encapsulation method.

There is no information about the introduced filler rates or the packaging material. The most distinctive feature that distinguishes the product of the invention disclosed in this specification from other bee products is that this is a fermented product. The fact that it has fermentation by-products in addition to all biological active substances present in other bee products makes bee bread valuable. It is not similar to the product disclosed in the mentioned patent documentin terms of bee product content, production method and usage patterns.

Patent publication No. WO2015079419 (A1) relates to the production of polymer-based porous membrane with antimicrobial active material additive in the range of −40° C./−400° C. and then by applying high pressure (60-350 bar) and in supercritical carbon dioxide environment. Herein, the rate of antimicrobial active material ranges from 0.001% to 50% by weight. Although the patent content includes antimicrobial products (bacteriocins, fungicides), the decription does not mention any fermented product related to bee bread or similar.

The aforementioned patent document includes the production of a polymer that is active only in terms of antimicrobial activity, especially advantageous to use as packaging material. Our patent application includes the production of a unique biocomposite material with the contribution of bee bread and the production of a non-toxic, biocompatible composite for the design of biomaterials to be used in tissue engineering and medical fields, especially in cardiovascular surgery, which has important features in terms of both antimicrobial and biological activity.

The patent application no TR 2019/09888 is related to obtaining a new fermented and probiotic milk product using bee bread and its production method. This application differs from the subject of the invention in terms of its production method and usage areas. While a product to be consumed directly is presented in the application, our invention discloses a bee bread product in the form of a fermented and biologically active substance that can be added to all products in food and health fields or to the packaging of products requiring high hygiene.

In the prior art, there are publications and patents related to biocomposite nanofiber produced with propolis by electrospinning method. However, having a different chemical composition from propolis, having high antioxidant capacity and strong antimicrobial activity are highlighting the bee bread. In addition, there is a difference in the extraction method of active biological components with this invention. The use of the extracts obtained in the production of biocomposite by lyophilization provides a very important advantage in the protection of active compounds.

In other methods; the biocomposite was produced after propolis, which is a poorly soluble and sticky product, is generally added not directly into the polymer solution, but after being dissolved in the solvent in which the polymer was dissolved. In addition, in some studies, during electrospinning process propolis extract and polymer are prepared with a solvent mixture consisting of two different solvents in order to use solutions in which propolis dissolves better and to provide a more homogeneous production which makes the process difficult. Solubility problems are experienced in the solvent used to dissolve the polymer and a rough composite is produced. At the same time, antimicrobial compounds cannot be fully transferred to these solvents.

As a result, a unique biocomposite material production with bee bread additive eliminating the disadvantages existing in the current technique for polymer biocomposite design, which has important properties in terms of both antimicrobial and biological activity, to be used in tissue engineering and medical fields, especially in cardiovascular surgery by the need to manufacture a non-toxic, biocompatible composite and the lack of existing solutions has made it compulsory to make an improvement in the related technical field.

Objectives and Short Description of the Invention

Bee bread is a product that known and used in traditional public health for many years and has attracted attention with its high nutritional value in recent years. Bee bread is a bee product made from pollen that is collected by the bees, mixed with digestive enzymes and carried back to the hive, made into pellets and protected with a small amount of honey and beeswax. The mixture prepared by bees undergoes fermentation under the influence of enzymes, microorganisms, humidity and temperature and is called bee bread after 2 weeks. The most distinctive feature that distinguishes this product from other bee products is that it is a fermented product.

The fact that it has fermentation by-products in addition to all biological active substances present in other bee products makes bee bread valuable.

Bee bread is actually a naturally fermented and preserved form of pollen. The biological activity of pollen decreases within 2 or 3 months after storage. In bee bread, activity is preserved for a long time. Pollen has many properties such as antimicrobial, antioxidant, hepatoprotective, immune modulator, anti-radiation and adaptogenic. It stimulates the human body, regulates metabolism, and exerts positive effects on liver, nervous system and endocrine system functions, increases tissue regeneration, physical and mental capacity. Bee bread also shows similar properties with pollen, moreover, the fact that the components in bee bread are partially fermented and can be easily assimilated into the organism makes its use more effective and advantageous.

The German Federal Ministry of Health officially recognized bee pollen as a medicine (Linskens and Jorde, 1997). Bee bread contains all the active biological compounds in normal pollen and it is also considered to be more valuable for human consumption than raw pollen. In addition, the presence of some honey and bee enzymes accompanying the pollen in the composition of bee bread strengthens its antimicrobial, anti-inflammatory, antioxidant hepato-renal protective activities.

Recent studies have reported that bee bread has a strong antimicrobial effect. It is stated that this effect is caused by compounds with antioxidant properties. Especially the high ratio of quarcetin and campherol in its composition contributes significantly to this effect. These compounds cause disruption of cell wall integrity, blockage of ion channels and inhibition of adenosintriphosphat synthesis (ATP) in the cell. In this respect, it has a natural antimicrobial effect. In addition, it is thought that the same mechanism is effective in preventing or slowing down the activities of precancerous and/or cancerous cells, so that it can be applied locally or systemically in almost any tissue with hyperplasia.

In addition, due to the metabolites (diacetyl, acetoin, acetaldehyde, bacteriocins) released as a result of lactic acid fermentation in bee bread and the pH decrease, the antimicrobial effect is further strengthened.

Therefore, the main aim of the invention is to obtain a polymer composite product with a more effective antimicrobial property by using bee bread rich in biological active compounds and to use this product in every field that requires antibacterial properties, mainly in the field of food and health.

Another aim of the invention is to provide bee bread extraction by using organic solvents from which biological active substances are extracted best, then by performing the extraction without damaging active biological compounds (by lyophilization) and to eliminate the solubility problem of these components. In this invention, the method and solvent in which the antimicrobial compounds present in bee bread can be extracted best are used. Thus, by using a natural antimicrobial product, the antimicrobial property of the polymer has been developed.

In addition, it is aimed to protect especially antimicrobial compounds by lyophilization. With this method, it was determined that the lyophilized extract dissolved better and the biocomposite obtained was provided to form a more homogeneous structure. In addition, the conditions (solvent, process parameters) that can be most suitable for electrospinning process and provide optimum properties are determined.

Bee bread is a fermented product with strong antimicrobial effect among bee products. A related aim of the invention is to further increase the targeted antimicrobial activity with antimicrobial compounds that may come from fermentation. In this respect, it stands out also with its therapeutic effects.

In order to achieve the above aims, the invention is a method of obtaining biocomposite nanofibers and includes the following steps:
  obtaining an extract by extracting bee bread,
  lyophilization (freeze-drying) of the extract,
  turning the thermoplastic polymer into a polymer solution with a magnetic stirrer,
  adding lyophilized bee bread extract into the polymer solution and obtaining a homogeneous solution with magnetic stirrer,
  converting the solution consisting of polymer and bee bread extract into nanofiber (biocomposite) by electrospinning method.

In the method suitable for this purpose, in the extraction process of bee bread, a mixture of 20-50% bee bread and methanol: water (80:20) is used and the extraction process is carried out in a shaking water bath at 50° C. for 10 hours. Subsequently, bee bread remaining on the filter in the first extraction process, is extracted 2 more times for one hour and a dense bee bread extract is obtained.

In this method, the bee bread extract obtained in mentioned extraction stage is frozen at −80° C., then freeze-dried in a lyophilizer and lyophilized by this way.

The thermoplastic polymer suitable for the method is preferably selected from polyurethane, polylactic acid, polyglycolic acid, poly(epsilon-caprolactone), polyethylene. The polymer solution is prepared in a homogeneous structure in the range of 6-15% by weight with a magnetic stirrer for 24 hours at room temperature. Subsequently, 5-50% by weight of lyophilized bee bread extract is added to the total polymer solution.

The obtained polymer solution and lyophilized bee bread extract mixture is subjected to stirring with a magnetic stirrer for 1-2 hours at room temperature to ensure a homogeneous structure.

The thermoplastic polymer solution reinforced with bee bread extract prepared at room temperature according to the invention is filled into a plastic syringe in the range of 10 mL-20 mL and is turned into nanofibers by feeding it to an electrospinning device through a stainless-steel needle.

At this stage, while the electrospinning solution feeding rate is in the range of 1 ml/min-20 mL/min, the distance between the needle tip and the collecting surface in electrospinning is between 5 cm-20 cm. The nanofibers obtained by electrospinning are wrapped in a rotating collector surface covered with an aluminum film.

The invention is also a biocomposite nanofiber produced using the method mentioned above.

Relevant biocomposite nanofiber is used as the main or intermediate raw material in areas requiring hygiene such as medical materials, packaging, food coating production, and textile, automotive, furniture and chemistry fields.

The mentioned biocomposite nanofiber can be applied locally in the field of health, especially for artificial vessels, prostheses, tissue support materials, bleeding stopping materials, wound care products used in wound infections and open wounds, and can also be used systemically as the main or intermediate raw material to balance the immune system in immunosuppressive or transplant patients.

DETAILED DESCRIPTION OF THE INVENTION

The invention is a polymer biocomposite product with high microbial activity obtained using bee bread, the method of obtaining this product and its use for coating material or as an intermediate raw material for artificial materials, packaging, etc. to be used in areas requiring hygiene.

The basic steps of the proposed method are as follows:
1—obtaining an extract by extracting bee bread,
2—lyophilization of (freeze-drying) extract,
3—bringing the thermoplastic polymer (preferably polyurethane, polylactic acid, polyglycolic acid, poly(epsilon-caprolactone), polyethylene) into solution with magnetic stirrer,
4—adding the polymer solution into lyophilized bee bread extract and obtaining a homogeneous solution with magnetic stirrer,
5—converting the solution consisting of polymer and bee bread extract into nanofibers (biocomposite) by electrospinning method,
6—using of the obtained biocomposite material as a coating or intermediate raw material for artificial materials, packaging, and etc. products that wanted to gain hygienic properties.

In the extraction process to be carried out in the first step, 20-50% bee bread is left to extraction with methanol: water (80:20) at 50° C. for 10 hours in a shaking water bath. At the end of the period, it is filtered through Whatman 1 filter. The bee bread remaining on the filter is left to be extracted with the same amount of solvent (methanol: water) for 1 hour under similar conditions, then the extract is removed by filtering through the filter paper. In the last stage, bee bread is left for 1 more hour extraction under similar conditions. The extracts obtained at the end of the three stages are combined. Then the methanol is removed by keeping it in the rotary evaporator under vacuum.

In the lyophilization stage of the method, the remaining dense extract is frozen at −80° C. and then freeze-dried in a lyophilizer. Lyophilization process is carried out in 3 main stages;
1. Freezing the Product: The process of completely freezing the product after passing through the appropriate pre-preparation processes, turning it into crystal form.
2. Sublimation (Primary Drying): Creating the energy required for sublimation to take place in the frozen product and performing sublimation. The stage where the water content is 90-95% removed.
3. Desorption (Secondary Drying): The process of removing water that cannot be removed in primary drying and is bound to the substance.

In the third step, the polymer is brought into solution using magnetic stirrer to prepare the polymer. Thermoplastic polymer (preferably polyurethane, polylactic acid, polyglycolic acid, poly (epsilon-caprolactone), polyethylene) is preferred as the polymer here.

The reason why the mentioned thermoplastic polyurethane material preferred is to have the properties of softening when heated, hardening when cooled, and being easily processed in heat-treatment processes such as extrusion and injection.

Furthermore, it shows a good performance during processing with its unique molecular structure and it can have different chemical properties and strengths by regulating the chemical structures in its formulation. This structure makes it a good packaging material.

In the fourth step, lyophilized bee bread extract is added to the polymer solution and a homogeneous solution is obtained with magnetic stirrer.

In the fifth step, this homogeneous solution (polymer, bee bread extract, solvent used to form the polymer solution) is transformed into nanofibers (biocomposite) by electrospinning method.

The above thermoplastic polymer solutions can be selected from solvents such as dimethyl sulfoxide or dimethyl formamide, as well as solvents such as tetrahydrofuran, acetone, methyl ethyl ketone, chloromethane, dichloromethane can be used to form the polymer solution.

In the preferred embodiment of the invention, lyophilized bee bread extract was prepared into a total polymer solution up to 50% by weight, by the following method: In the first step, a homogeneous polymer solution (in the range of 6-15% by weight) is prepared with magnetic stirrer for 24 hours at room temperature. In the second stage, 5-50% by weight of lyophilized bee bread extract is added into the total polymer solution and mixing continues with magnetic stirrer at room temperature for 1-2 hours until a homogeneous structure is obtained.

Bee bread extract added thermoplastic polymer solutions prepared at room temperature, are filled into a plastic syringe in the range of 10 mL-20 mL and this syringe is attached to a stainless-steel needle used as a nozzle. The polymer solution in the syringe is produced in the form of nanofibers by using an electrospinning device (Inovenso-Nanospinner24). Here, the emitter electrode of the high-voltage power supply, which will allow the polymer solution to be drawn into fibers, is charged by connecting it to a conductive jet. The other or grounding electrode of the high-voltage power supply is connected to the conductor collecting device to complete the cycle. To adjust the optimum voltage for each polymer solution, different voltages were applied to the polymer solutions obtained as nanofibers by electrospinning. The feeding rate was set as 1 mL/min-20 mL/min and the distance between the needle tip and the collector surface was set as 5 cm-20 cm. The samples (Nanofibers) are wrapped in a collector surface covered with an aluminum film and in rotation.

The recommended packaging material is the use of pollen, propolis, honey, brood homogenate, as well as biologically active products including vitamins, food coloring, mineral and medicinal substances in the form of wax. The product also allows for effective oral or sublingual use. The product can be used as food, packaging, medical products (all implant materials remaining in the body) by covering them with appropriate coating techniques. For example, it can be applied locally in artificial vessels, prostheses, tissue support materials, hemorrhage stopping materials, wound infections and wound care products, open wounds, as well as it is used systemically for balancing the immune system in immunosuppressive or transplant patients, textile, automotive, furniture, chemistry fields.

The invention claimed is:

1. A method of producing a biocomposite nanofiber, the method comprising:
    extracting bee bread so as to obtain an extract;
    lyophilizing of the extract;
    turning a thermoplastic polymer into a polymer solution by using a magnetic stirrer;
    adding the lyophilized extract into the polymer solution;
    stirring the added lyophilized extract and the polymer solution with the magnetic stirrer so as to obtain a homogenous solution; and
    electrospinning the homogenous solution so as to form the biocomposite nanofiber.

2. The method of claim 1, wherein the bee bread has a mixture of 20% to 50% bee bread with methanol, wherein the step of extracting comprises:
    extracting the bee bread with water.

3. The method of claim 1, wherein the step of extracting in carried out at 50° C. for ten hours in a shaken water bath.

4. The method of claim 1, wherein the step of extracting the bee bread comprises:
    filtering the bee bread with a filter at least two times for one hour so as to obtain the extract.

5. The method of claim 1, further comprising:
    freezing the extract at a temperature of −80° C., wherein the step of lyophilizing is carried out in lyophilizer.

6. The method of claim 1, wherein the thermoplastic polymer is selected from the group consisting of polyurethane, polylactic acid, polyglycolic acid, poly (epsilon-caprolactone), and polyethylene.

7. The method of claim 1, wherein the step of turning comprises:
    preparing the polymer solution in a homogenous structure with the magnetic stirrer for twenty-four hours at room temperature.

8. The method of claim 1, wherein the step of adding the lyophilized extract into the polymer solution comprises:
    adding 5% to 50% lyophilized extract to the polymer solution.

9. The method of claim 1, wherein the step of stirring comprises:
    stirring the added lyophilized extract and the polymer solution for between one hour and two hours at room temperature.

10. The method of claim 1, further comprising:
    filling a plastic syringe with ten milliliters to twenty milliliters of solution.

11. The method of claim 10, wherein the step of electrospinning comprises:
    passing the homogenous solution from the plastic syringe through a stainless steel needle into an electrospinning device.

12. The method of claim 11, wherein the step of passing is at a rate of between one milliliter per minute and twenty milliliters per minute.

13. The method of claim 12, wherein a tip of the stainless steel needle is spaced by five centimeters to twenty centimeters from a collector surface of the electrospinning device.

14. The method of claim 1, further comprising:
    winding the biocomposite nanofiber onto a collector surface by rotating the collector surface, the collector surface being covered with an aluminum film.

15. A biocomposite nanofiber produced by the method of claim 1.

* * * * *